(12) United States Patent
Pless et al.

(10) Patent No.: US 9,554,694 B2
(45) Date of Patent: *Jan. 31, 2017

(54) INTEGRATED DELIVERY AND VISUALIZATION TOOL FOR A NEUROMODULATION SYSTEM

(71) Applicant: Autonomic Technologies, Inc., Redwood City, CA (US)

(72) Inventors: Benjamin David Pless, Atherton, CA (US); Carl Lance Boling, San Jose, CA (US); Anthony V. Caparso, San Jose, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/312,142

(22) Filed: Jun. 23, 2014

(65) Prior Publication Data

US 2014/0303436 A1 Oct. 9, 2014

Related U.S. Application Data

(60) Continuation of application No. 13/784,452, filed on Mar. 4, 2013, now Pat. No. 8,781,574, which is a
(Continued)

(51) Int. Cl.
*A61B 1/07* (2006.01)
*A61B 1/00* (2006.01)
(Continued)

(52) U.S. Cl.
CPC ............. *A61B 1/07* (2013.01); *A61B 1/00135* (2013.01); *A61B 1/00154* (2013.01);
(Continued)

(58) Field of Classification Search
None
See application file for complete search history.

(56) References Cited

U.S. PATENT DOCUMENTS 2,123,980 A 7/1938 Warwick
2,182,071 A 12/1939 Crossley
(Continued)

FOREIGN PATENT DOCUMENTS

EP 69427 A2 1/1983
EP 0970813 A2 1/2000
(Continued)

OTHER PUBLICATIONS

Alstadhaug, K.B.; Migraine and the hypothalamus; Cephalalgia (Blackwell Publishing Ltd.); pp. 1-9; Aug. 2009.
(Continued)

*Primary Examiner* — Paula J Stice
(74) *Attorney, Agent, or Firm* — Tarolli, Sundheim, Covell & Tummino LLP

(57) ABSTRACT

Methods and apparatus for delivering a neurostimulator to a target tissue are provided which may include any number of features. One feature is a delivery tool comprising a handle portion, an elongate shaft comprising a contoured distal portion, a visualization system embedded in the elongate shaft, and an insertion groove on the elongate shaft configured to deploy the neurostimulator. The contoured distal portion can be shaped and configured to maintain contact with a posterior maxilla and elevate a periosteum off of the posterior maxilla to avoid soft tissue dissection. In some embodiments, the neurostimulator is implanted in close proximity to or touching the sphenopalatine ganglion.

18 Claims, 8 Drawing Sheets

Related U.S. Application Data division of application No. 12/649,119, filed on Dec. 29, 2009, now Pat. No. 8,412,336.

(60) Provisional application No. 61/141,179, filed on Dec. 29, 2008.

(51) Int. Cl.

| | | |
|---|---|---|
| *A61B 1/015* | (2006.01) | |
| *A61B 1/018* | (2006.01) | |
| *A61B 1/04* | (2006.01) | |
| *A61B 1/313* | (2006.01) | |
| *A61N 1/36* | (2006.01) | |
| *A61N 1/372* | (2006.01) | |

(52) U.S. Cl.
CPC .............. *A61B 1/015* (2013.01); *A61B 1/018* (2013.01); *A61B 1/042* (2013.01); *A61B 1/313* (2013.01); *A61N 1/36082* (2013.01); *A61B 1/00165* (2013.01); *A61N 1/36071* (2013.01); *A61N 1/36114* (2013.01); *A61N 1/37205* (2013.01)

(56) References Cited

U.S. PATENT DOCUMENTS

| | | |
|---|---|---|
| 3,357,434 A | 12/1967 | Abell |
| 3,746,004 A | 7/1973 | Jankelson |
| 3,859,103 A * | 1/1975 | Yoshiyagawa et al. ...... 385/124 |
| 3,862,321 A | 1/1975 | Adams et al. |
| 3,914,283 A | 10/1975 | Okamoto et al. |
| 3,923,060 A | 12/1975 | Ellinwood, Jr. |
| 3,925,469 A | 12/1975 | Adams et al. |
| 4,073,917 A | 2/1978 | Sandberg et al. |
| 4,102,344 A | 7/1978 | Conway et al. |
| 4,117,160 A | 9/1978 | Molnar et al. |
| 4,147,804 A | 4/1979 | Diamond et al. |
| 4,217,349 A | 8/1980 | Katsube et al. |
| 4,298,603 A | 11/1981 | Chang et al. |
| 4,305,402 A | 12/1981 | Katims |
| 4,352,820 A | 10/1982 | Scurlock et al. |
| 4,379,161 A | 4/1983 | Thominet et al. |
| 4,397,845 A | 8/1983 | Allen |
| 4,441,210 A | 4/1984 | Hochmair et al. |
| 4,495,174 A | 1/1985 | Allcock et al. |
| 4,519,400 A | 5/1985 | Brenman et al. |
| 4,529,601 A | 7/1985 | Broberg et al. |
| 4,550,733 A | 11/1985 | Liss et al. |
| 4,551,453 A | 11/1985 | Marsili |
| 4,565,200 A | 1/1986 | Cosman |
| 4,592,359 A | 6/1986 | Galbraith |
| 4,622,219 A | 11/1986 | Haynes |
| 4,627,438 A | 12/1986 | Liss et al. |
| 4,632,940 A | 12/1986 | Chiarino et al. |
| 4,646,744 A | 3/1987 | Capel |
| 4,692,147 A | 9/1987 | Duggan |
| 4,695,576 A | 9/1987 | Ekenstam et al. |
| 4,718,423 A | 1/1988 | Willis et al. |
| 4,727,145 A | 2/1988 | Press |
| 4,784,142 A | 11/1988 | Liss et al. |
| 4,830,008 A | 5/1989 | Meer |
| 4,833,149 A | 5/1989 | Press |
| 4,856,526 A | 8/1989 | Liss et al. |
| 4,870,086 A | 9/1989 | Sandberg |
| 4,871,475 A | 10/1989 | Lubowitz et al. |
| 4,886,493 A | 12/1989 | Yee |
| 4,920,979 A | 5/1990 | Bullara |
| 4,937,078 A | 6/1990 | Mezei et al. |
| 5,038,781 A | 8/1991 | Lynch |
| 5,085,868 A | 2/1992 | Mattsson et al. |
| 5,178,156 A | 1/1993 | Takishima et al. |
| 5,193,539 A | 3/1993 | Schulman et al. |
| 5,199,428 A | 4/1993 | Obel et al. |
| 5,215,086 A | 6/1993 | Terry, Jr. et al. |
| 5,227,165 A | 7/1993 | Domb et al. |
| 5,234,957 A | 8/1993 | Mantelle |
| 5,255,691 A | 10/1993 | Otten |
| 5,259,387 A | 11/1993 | dePinto |
| 5,314,458 A | 5/1994 | Najafi |
| 5,330,515 A | 7/1994 | Rutecki et al. |
| 5,335,657 A | 8/1994 | Terry, Jr. et al. |
| 5,344,438 A | 9/1994 | Testerman et al. |
| 5,360,805 A | 11/1994 | Ask et al. |
| 5,387,587 A | 2/1995 | Hausler et al. |
| 5,411,546 A | 5/1995 | Bowald et al. |
| 5,420,151 A | 5/1995 | Hammarberg et al. |
| 5,428,006 A | 6/1995 | Bechgaard et al. |
| 5,433,739 A | 7/1995 | Sluijter et al. |
| 5,458,631 A | 10/1995 | Xavier |
| 5,490,520 A | 2/1996 | Schaefer et al. |
| 5,514,131 A | 5/1996 | Edwards et al. |
| 5,540,730 A | 7/1996 | Terry, Jr. et al. |
| 5,540,734 A | 7/1996 | Zabara |
| 5,545,219 A | 8/1996 | Kuzma |
| 5,558,622 A | 9/1996 | Greenberg |
| 5,560,351 A * | 10/1996 | Gravenstein et al. ... 128/200.26 |
| 5,569,166 A | 10/1996 | Stone |
| 5,578,061 A | 11/1996 | Stroetmann et al. |
| 5,591,216 A | 1/1997 | Testerman et al. |
| 5,640,764 A | 6/1997 | Strojnik |
| 5,645,570 A | 7/1997 | Corbucci |
| 5,653,734 A | 8/1997 | Alt |
| 5,658,318 A | 8/1997 | Stroetmann et al. |
| 5,660,837 A | 8/1997 | Lundquist |
| 5,676,955 A | 10/1997 | Ansmann et al. |
| 5,690,692 A | 11/1997 | Fleming |
| 5,700,282 A | 12/1997 | Zabara |
| 5,711,316 A | 1/1998 | Elsberry et al. |
| 5,713,922 A | 2/1998 | King |
| 5,735,817 A | 4/1998 | Shantha |
| 5,756,520 A | 5/1998 | Ask et al. |
| 5,766,605 A | 6/1998 | Sanders et al. |
| 5,824,027 A | 10/1998 | Hoffer et al. |
| 5,843,021 A | 12/1998 | Edwards et al. |
| 5,861,014 A | 1/1999 | Familoni |
| 5,865,843 A | 2/1999 | Baudino |
| 5,938,688 A | 8/1999 | Schiff |
| 6,001,088 A | 12/1999 | Roberts et al. |
| 6,006,134 A | 12/1999 | Hill et al. |
| 6,016,449 A | 1/2000 | Fischell et al. |
| 6,026,326 A | 2/2000 | Bardy |
| 6,058,331 A | 5/2000 | King |
| 6,073,048 A | 6/2000 | Kieval et al. |
| 6,093,145 A | 7/2000 | Vom Berg et al. |
| 6,094,598 A | 7/2000 | Elsberry et al. |
| 6,104,957 A | 8/2000 | Alo et al. |
| 6,128,538 A | 10/2000 | Fischell et al. |
| 6,132,384 A | 10/2000 | Christopherson et al. |
| 6,134,474 A | 10/2000 | Fischell et al. |
| 6,141,590 A | 10/2000 | Renirie et al. |
| 6,146,380 A | 11/2000 | Racz et al. |
| 6,161,044 A | 12/2000 | Silverstone |
| 6,161,048 A | 12/2000 | Sluijter et al. |
| 6,178,349 B1 | 1/2001 | Kieval |
| 6,205,359 B1 | 3/2001 | Boveja |
| 6,246,912 B1 | 6/2001 | Sluijter et al. |
| 6,251,126 B1 | 6/2001 | Ottenhoff et al. |
| 6,259,952 B1 | 7/2001 | Sluijter et al. |
| 6,262,377 B1 | 7/2001 | Nielsen et al. |
| 6,269,270 B1 | 7/2001 | Boveja |
| 6,292,695 B1 | 9/2001 | Webster, Jr. et al. |
| 6,308,105 B1 | 10/2001 | Duysens et al. |
| 6,353,762 B1 | 3/2002 | Murthy |
| 6,356,786 B1 | 3/2002 | Rezai et al. |
| 6,356,787 B1 | 3/2002 | Rezai et al. |
| 6,356,788 B2 | 3/2002 | Boveja |
| 6,366,814 B1 | 4/2002 | Boveja et al. |
| 6,400,982 B2 | 6/2002 | Sweeney et al. |
| 6,405,079 B1 | 6/2002 | Ansarinia |
| 6,432,986 B2 | 8/2002 | Levin |
| 6,438,423 B1 | 8/2002 | Rezai et al. |
| 6,456,786 B1 | 9/2002 | Uchida et al. |
| 6,458,157 B1 | 10/2002 | Suaning |

(56) References Cited

U.S. PATENT DOCUMENTS

| | | |
|---|---|---|
| 6,491,940 B1 | 12/2002 | Levin |
| 6,511,500 B1 | 1/2003 | Rahme |
| 6,526,318 B1 | 2/2003 | Ansarinia |
| 6,564,096 B2 | 5/2003 | Mest |
| 6,564,102 B1 | 5/2003 | Boveja |
| 6,610,713 B2 | 8/2003 | Tracey |
| 6,615,081 B1 | 9/2003 | Boveja |
| 6,633,779 B1 | 10/2003 | Schuler |
| 6,647,296 B2 | 11/2003 | Fischell et al. |
| 6,665,562 B2 | 12/2003 | Gluckman et al. |
| 6,668,191 B1 | 12/2003 | Boveja |
| 6,735,475 B1 | 5/2004 | Whitehurst et al. |
| 6,760,626 B1 | 7/2004 | Boveja |
| 6,788,975 B1 | 9/2004 | Whitehurst et al. |
| RE38,654 E | 11/2004 | Hill et al. |
| 6,819,956 B2 | 11/2004 | DiLorenzo |
| 6,832,114 B1 | 12/2004 | Whitehurst et al. |
| 6,853,858 B2 | 2/2005 | Shalev |
| 6,885,888 B2 | 4/2005 | Rezai |
| 6,978,180 B2 | 12/2005 | Tadlock |
| 7,003,352 B1 | 2/2006 | Whitehurst |
| 7,027,860 B2 | 4/2006 | Bruninga et al. |
| 7,047,078 B2 | 5/2006 | Boggs, II et al. |
| 7,076,307 B2 | 7/2006 | Boveja et al. |
| 7,113,033 B2 | 9/2006 | Barnett |
| 7,117,033 B2 | 10/2006 | Shalev et al. |
| 7,120,489 B2 | 10/2006 | Shalev et al. |
| 7,149,574 B2 | 12/2006 | Yun et al. |
| 7,167,751 B1 | 1/2007 | Whitehurst et al. |
| 7,191,012 B2 | 3/2007 | Boveja et al. |
| 7,203,548 B2 | 4/2007 | Whitehurst et al. |
| 7,209,787 B2 | 4/2007 | DiLorenzo |
| 7,277,758 B2 | 10/2007 | DiLorenzo |
| 7,285,118 B1 | 10/2007 | Lozano |
| 7,286,879 B2 | 10/2007 | Wallace |
| 7,292,890 B2 | 11/2007 | Whitehurst et al. |
| 7,340,298 B1 | 3/2008 | Barbut |
| 7,349,743 B2 | 3/2008 | Tadlock |
| 7,363,076 B2 | 4/2008 | Yun et al. |
| 7,369,897 B2 | 5/2008 | Boveja et al. |
| 7,403,821 B2 | 7/2008 | Haugland et al. |
| 7,477,945 B2 | 1/2009 | Rezai et al. |
| 7,494,458 B2 | 2/2009 | Fischell et al. |
| 7,532,938 B2 | 5/2009 | Machado et al. |
| 7,561,919 B2 | 7/2009 | Shalev et al. |
| 7,623,924 B2 | 11/2009 | Narciso, Jr. |
| 7,636,597 B2 * | 12/2009 | Gross et al. .................... 607/2 |
| 7,640,057 B2 | 12/2009 | Libbus et al. |
| 7,689,276 B2 | 3/2010 | Dobak |
| 7,763,034 B2 | 7/2010 | Siegel et al. |
| 7,778,704 B2 | 8/2010 | Rezai |
| 7,799,337 B2 | 9/2010 | Levin |
| 7,848,816 B1 | 12/2010 | Wenzel et al. |
| 7,865,237 B2 | 1/2011 | Machado et al. |
| 7,877,146 B2 | 1/2011 | Rezai |
| 8,046,075 B2 | 10/2011 | Rezai |
| 8,165,691 B2 | 4/2012 | Ellingson et al. |
| 8,195,297 B2 | 6/2012 | Penner |
| 8,206,369 B2 | 6/2012 | Ansarinia |
| 8,224,438 B2 | 7/2012 | Levin |
| 8,355,779 B2 | 1/2013 | Ansarinia |
| 8,412,336 B2 | 4/2013 | Pless et al. |
| 8,473,062 B2 | 6/2013 | Pless |
| 8,489,192 B1 | 7/2013 | Hlavka et al. |
| 8,494,641 B2 | 7/2013 | Boling et al. |
| 8,583,229 B2 | 11/2013 | Rezai et al. |
| 8,781,574 B2 | 7/2014 | Pless et al. |
| 2002/0026222 A1 | 2/2002 | Schauerte et al. |
| 2002/0073334 A1 | 6/2002 | Sherman et al. |
| 2002/0107553 A1 | 8/2002 | Hill et al. |
| 2002/0169365 A1 | 11/2002 | Nakada et al. |
| 2003/0004549 A1 | 1/2003 | Hill et al. |
| 2003/0018367 A1 | 1/2003 | DiLorenzo |
| 2003/0018368 A1 | 1/2003 | Ansarinia |
| 2003/0028147 A1 * | 2/2003 | Aves et al. .............. 604/164.06 |
| 2003/0060857 A1 | 3/2003 | Perrson et al. |
| 2003/0065374 A1 | 4/2003 | Honeck |
| 2003/0100924 A1 | 5/2003 | Foreman et al. |
| 2003/0144709 A1 | 7/2003 | Zabara et al. |
| 2003/0176898 A1 | 9/2003 | Gross et al. |
| 2003/0181951 A1 | 9/2003 | Cates |
| 2003/0181958 A1 | 9/2003 | Dobak, III |
| 2003/0181959 A1 | 9/2003 | Dobak, III |
| 2003/0212440 A1 | 11/2003 | Boveja |
| 2003/0216792 A1 | 11/2003 | Levin et al. |
| 2004/0015204 A1 | 1/2004 | Whitehurst et al. |
| 2004/0093053 A1 | 5/2004 | Gerber et al. |
| 2004/0172084 A1 | 9/2004 | Knudson et al. |
| 2004/0230255 A1 | 11/2004 | Dobak, III |
| 2004/0236381 A1 | 11/2004 | Dinsmoor et al. |
| 2005/0038484 A1 | 2/2005 | Knudson et al. |
| 2005/0075701 A1 | 4/2005 | Shafer |
| 2005/0075702 A1 | 4/2005 | Shafer |
| 2005/0102006 A1 | 5/2005 | Whitehurst et al. |
| 2005/0143378 A1 | 6/2005 | Yun et al. |
| 2005/0143626 A1 * | 6/2005 | Prescott ................... 600/162 |
| 2005/0143787 A1 | 6/2005 | Boveja et al. |
| 2005/0149156 A1 | 7/2005 | Libbus et al. |
| 2005/0153885 A1 | 7/2005 | Yun et al. |
| 2005/0154419 A1 | 7/2005 | Whitehurst et al. |
| 2005/0154426 A1 | 7/2005 | Boveja et al. |
| 2005/0159790 A1 | 7/2005 | Shalev |
| 2005/0209654 A1 | 9/2005 | Boveja et al. |
| 2005/0216070 A1 | 9/2005 | Boveja et al. |
| 2005/0234523 A1 | 10/2005 | Levin et al. |
| 2005/0281751 A1 | 12/2005 | Levin |
| 2006/0004423 A1 | 1/2006 | Boveja et al. |
| 2006/0020299 A1 | 1/2006 | Shalev |
| 2006/0064140 A1 | 3/2006 | Whitehurst et al. |
| 2006/0074450 A1 | 4/2006 | Boveja et al. |
| 2006/0074463 A1 | 4/2006 | Seeberger et al. |
| 2006/0079945 A1 | 4/2006 | Libbus |
| 2006/0085046 A1 | 4/2006 | Rezai |
| 2006/0095088 A1 | 5/2006 | De Ridder |
| 2006/0100668 A1 | 5/2006 | Ben-David et al. |
| 2006/0100671 A1 | 5/2006 | De Ridder |
| 2006/0106285 A1 * | 5/2006 | Boulais et al. .............. 600/156 |
| 2006/0116721 A1 | 6/2006 | Yun et al. |
| 2006/0122660 A1 | 6/2006 | Boveja et al. |
| 2006/0149337 A1 | 7/2006 | John |
| 2006/0167497 A1 | 7/2006 | Armstrong et al. |
| 2006/0173495 A1 | 8/2006 | Armstrong et al. |
| 2006/0178666 A1 | 8/2006 | Cosman et al. |
| 2006/0184211 A1 | 8/2006 | Gaunt et al. |
| 2006/0206165 A1 | 9/2006 | Jaax et al. |
| 2006/0235484 A1 | 10/2006 | Jaax et al. |
| 2006/0287678 A1 | 12/2006 | Shafer |
| 2006/0293723 A1 | 12/2006 | Whitehurst et al. |
| 2007/0021801 A1 | 1/2007 | Heruth et al. |
| 2007/0021802 A1 | 1/2007 | Heruth et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027498 A1 | 2/2007 | Maschino et al. |
| 2007/0039625 A1 | 2/2007 | Heruth et al. |
| 2007/0049988 A1 | 3/2007 | Carbunaru et al. |
| 2007/0066997 A1 | 3/2007 | He et al. |
| 2007/0067004 A1 | 3/2007 | Boveja et al. |
| 2007/0083245 A1 | 4/2007 | Lamensdorf et al. |
| 2007/0100411 A1 | 5/2007 | Bonde |
| 2007/0106143 A1 | 5/2007 | Flaherty |
| 2007/0112404 A1 | 5/2007 | Mann et al. |
| 2007/0142875 A1 * | 6/2007 | Shalev et al. ................ 607/45 |
| 2007/0156177 A1 | 7/2007 | Harel et al. |
| 2007/0156179 A1 | 7/2007 | S.E. |
| 2007/0203521 A1 | 8/2007 | Dobak et al. |
| 2007/0233193 A1 | 10/2007 | Craig |
| 2007/0250119 A1 | 10/2007 | Tyler et al. |
| 2007/0250145 A1 | 10/2007 | Kraus et al. |
| 2007/0255368 A1 | 11/2007 | Bonde et al. |
| 2007/0255369 A1 | 11/2007 | Bonde et al. |
| 2007/0293906 A1 | 12/2007 | Cowan et al. |
| 2008/0021341 A1 | 1/2008 | Harris et al. |
| 2008/0027346 A1 | 1/2008 | Litt et al. |

(56) References Cited

U.S. PATENT DOCUMENTS

| | | |
|---|---|---|
| 2008/0033509 A1 | 2/2008 | Shalev et al. |
| 2008/0046053 A1 | 2/2008 | Wagner et al. |
| 2008/0071318 A1 | 3/2008 | Brooke et al. |
| 2008/0086182 A1 | 4/2008 | Ben-David et al. |
| 2008/0103547 A1 | 5/2008 | Okun et al. |
| 2008/0103569 A1 | 5/2008 | Gerber |
| 2008/0132933 A1 | 6/2008 | Gerber |
| 2008/0132981 A1 | 6/2008 | Gerber |
| 2008/0132982 A1 | 6/2008 | Gerber |
| 2008/0140000 A1 | 6/2008 | Shuros et al. |
| 2008/0161877 A1 | 7/2008 | Kirby et al. |
| 2008/0161894 A1 | 7/2008 | Ben-David et al. |
| 2008/0183237 A1 | 7/2008 | Errico et al. |
| 2008/0183246 A1 | 7/2008 | Patel et al. |
| 2008/0183253 A1 | 7/2008 | Bly |
| 2008/0221921 A1 | 9/2008 | Love et al. |
| 2008/0262566 A1 | 10/2008 | Jaax |
| 2008/0269716 A1 | 10/2008 | Bonde et al. |
| 2009/0012577 A1 | 1/2009 | Rezai et al. |
| 2009/0036949 A1 | 2/2009 | Kokones et al. |
| 2009/0105783 A1 | 4/2009 | Solberg et al. |
| 2009/0118780 A1 | 5/2009 | DiLorenzo |
| 2009/0264956 A1 | 10/2009 | Rise et al. |
| 2009/0276025 A1 | 11/2009 | Burnes et al. |
| 2009/0312817 A1 | 12/2009 | Hogle et al. |
| 2009/0320845 A1 | 12/2009 | Fishman et al. |
| 2010/0179617 A1 | 7/2010 | Fletcher et al. |
| 2010/0185249 A1 | 7/2010 | Wingeier et al. |
| 2010/0185258 A1 | 7/2010 | Papay |
| 2010/0211123 A1 | 8/2010 | Stubbs et al. |
| 2010/0228316 A1 | 9/2010 | Errico et al. |
| 2010/0228318 A1 | 9/2010 | Errico et al. |
| 2010/0268306 A1 | 10/2010 | Maniak et al. |
| 2010/0305664 A1 | 12/2010 | Wingeier et al. |
| 2011/0029037 A1 | 2/2011 | Rezai et al. |
| 2011/0046432 A1 | 2/2011 | Simon et al. |
| 2011/0125214 A1 | 5/2011 | Goetz et al. |
| 2011/0125215 A1 | 5/2011 | Goetz et al. |
| 2012/0209286 A1 | 8/2012 | Papay et al. |
| 2012/0270876 A1 | 10/2012 | Yun et al. |
| 2013/0110195 A1 | 5/2013 | Fletcher et al. |
| 2013/0116745 A1 | 5/2013 | Fletcher et al. |
| 2013/0131636 A1 | 5/2013 | Rezai et al. |
| 2013/0178829 A1 | 7/2013 | Rezai et al. |
| 2013/0296993 A1 | 11/2013 | Boling et al. |
| 2014/0207220 A1 | 7/2014 | Boling et al. |

FOREIGN PATENT DOCUMENTS

| | | |
|---|---|---|
| EP | 754060 B1 | 3/2003 |
| RU | 2108817 C1 | 4/1996 |
| WO | WO85/00599 A1 | 2/1985 |
| WO | WO92/07605 A1 | 5/1992 |
| WO | WO95/21821 A1 | 8/1995 |
| WO | WO97/02000 A1 | 1/1997 |
| WO | WO97/15548 A1 | 5/1997 |
| WO | WO97/23467 A1 | 7/1997 |
| WO | WO97/38675 A1 | 10/1997 |
| WO | WO01/85094 A2 | 11/2001 |
| WO | WO01/97905 A1 | 12/2001 |
| WO | WO03/082123 A2 | 10/2003 |
| WO | WO2005/105202 A1 | 11/2005 |

OTHER PUBLICATIONS

Babe, "Treatment of sphenopalatine ganglion neuralgia", An Otorrinolaringol Ibero Am, vol. 16(5): 463-74 (year of pub. sufficiently earlier than effective US filed and any foreign priority date) 1989 (abstract).
Barre, "Cocaine as an abortive agent in cluster headache", Headache, vol. 22: 69-73 (Mar. 1982).
Benumof et al.; Pulmonary artery catheterization; In Clinical Procedures in Anesthesia and Intensive Care; JB Lippincott Company; pp. 405-441; (year of pub. sufficiently earlier than effective US filed and any foreign priority date) 1992.
Berger et al., "Does topical anesthesia of the sphenopalatine ganglion with cocaine or lidocaine relieve low back pain?", Anesth Analg, vol. 65(6); pp. 700-702; Jun. 1986.
Boysen et al.; Parasympathetic tonic dilatory influences on cerebral vessels; Autonomic Neuroscience: Basic and Clinical; vol. 147; pp. 101-104; Feb. 2009.
Browne et al., "Concurrent cervical and craniofacial pain" Oral Surg Oral Med Oral Path 86(6): 633-640 (Dec. 1998).
Carroll et al., "Motor cortex stimulation for chronic neuropathic pain: a preliminary study of 10 cases" Pain 84:431-437 (Feb. 2000).
Cepero et al., "Long-term results of sphenopalatine ganglioneurectomy for facial pain", Am J Otolaryngol, 8(3): 171-4 (May-Jun. 1987).
Cohen et al.; Sphenopalatine ganglion block for postdural puncture headache; Anaesthesia; vol. 64; pp. 574-575; May 2009.
Cook, "Cryosurgery of headache", Res Clin Stud Headache, vol. 5: 86-101 (year of pub. sufficiently earlier than effective US filed and any foreign priority date) 1978 (abstract).
Cooke-Ariel; Circadian variations in cardiovascular function and their relation to the occurrence and timing of cardiac events; Am. J. Heath. Syst. Pharm.; vol. 55; supp. 3; pp. S5-S11; Nov. 15, 1998.
Cooper et al.; Neural effects on sinus rate and atrioventricular conduction produced by electrical stimulation from a transvenous electrode catheter in the canine right pulmonary artery; Circulation Research; vol. 46; pp. 48-57; Jan. 1980.
Cutrer et al., "Effects of PNU-109,291, a selective 5H-T1D receptor agonist, on electrically induced dural plasma extravasation and capsaicin-evoked c-fos immunoreactivity within trigeminal nucleus caudalis" Neuropharm 38:1043-1053 (Jul. 1999).
Delepine et al., "Plasma protein extravasation induced in the rat dura mater by stimulation of the parasympathetic sphenopalatine ganglion", Exp Neurology, vol. 147: 389-400 (Oct. 1997).
Devoghel, "Cluster headache and sphenopalatine block", Acta Anaesthesio Belg, vol. 32(1), pp. 101-107 (year of pub. sufficiently earlier than effective US filed and any foreign priority date) 1981.
Feindel et al., "The tentorial nerves and localization of intracranial pain in man" Neurology; 10(6); pp. 555-563; Jun. 1960.
Ferrante et al., "Sphenopalatine ganglion block for the treatment of myofascial pain of the head, neck, and shoulders", Reg Anesth Pain, vol. 23(1): 30-6 (Jan.-Feb. 1998) (abstract).
Frisardi et al., "Electric versus magnetic transcranial stimulation of the trigeminal system in healthy subjects. Clinical applications in gnathology.", J Oral Rehabil, 24(12): 920-8; Dec. 1987 (abstract).
Giles; Importance of long-acting andiotensin-converting enzyme inhibitors for congestive heart failure; Am. J. Cardiol.; vol. 70; pp. 98C-101C; Oct. 8, 1992.
Goadsby et al., "Differential effects of low dose CP122,288 and eletriptan on Fos expression due to stimulation of the superior sagittal sinus in cat" Pain 82:15-22 (Jul. 1999).
Goadsby et al., "Stimulation of an intracranial trigeminally-innervated structure selectively increases cerebral blood flow" Brain Research 751:247-252 (Mar. 1997).
Goadsby et al., "Substance P blockade with the potent and centrally acting antagonist GR205171 does not effect central trigeminal activity with superior sagittal sinus stimuation" Neuroscience 86(1):337-343 (Sep. 1998).
Goadsby et al., "The trigeminovascular system and migraine: studies characterizing cerebrovascular and neuropeptide changes seen in humans and cats" Ann Neurol 33:48-56 (Jan. 1993).
Goadsby et al., Effect of stimulation of trigeminal ganglion on regional cerebral blood flow in cats; Am J. Physiol.; vol. 22; pp. R270-R274; Aug. 1987.
Goadsby, "Sphenopalatine ganglion stimulation increases regional blood flow independent of glucose utilization in the cat", Brain Research, vol. 506: 145-8 (Jan. 1990).
Gregoire, "Cluster headaches", Can Nurse, vol. 87(9): 33-5 (Oct. 1991) (abstract).
Gromova et al.; Sinusoidal modulated currents in comprehensive treatment of children with bronchial asthma; Voprosy Kurortologii Fizioterapii, I Lechebnoi Fizicheskoi Kultury; May-Jun.; (3); pp.

(56) References Cited

OTHER PUBLICATIONS 45-47; (year of pub. sufficiently earlier than effective US filed and any foreign priority date) 1981 (w/ English Abstract).
Grossmann; Effects of cardiac glycosides on 24-h ambulatory blood pressure in healthy volunteers and patients with heart failure; Eur J Clin Invest; vol. 31; Iss.S2; pp. 26-30; Apr. 2001.
Gudovsky et al.; Surgical treatment of bronchial asthma; Surgery (Khigurgiia); vol. 7; pp. 14-18; Jul. 2002.
Guo et al.; Treatment of primary trigeminal neuralgia with acupuncture at the sphenopalatine ganglion; Journal of traditional chinese medicine; vol. 15(1) pp. 31-33; Mar. 1995.
Hardebo, Jan-Erik; Activation of pain fibers to the internal carotid artery intracranially may cause the pain and local signs of reduced sympathetic and enhanced parasympathetic activity in cluster headache; Headache; 31; pp. 314-320; May 1991.
Hardebo, Jan-Erik; On pain mechanisms in cluster headache; Headache; 31; pp. 91-106; Feb. 1991.
Headache Classification Committee of the International Headache Society, "Classification and diagnostic criteria for headache disorders, cranial neuralgias and facial pain", Cephalalgia, Supp & 0:13, 19-24 and 35-38 (Feb. 1988).
Heusch et al.; Adrenergic mechanisms in myocardial ischemia; Supp. to Basic Research in Cardiology; vol. 85; (year of pub. sufficiently earlier than effective US filed and any foreign priority date) 1990.
Hillier; Monitored anesthesia care; Clinical Anesthesia; Ch. 47; pp. 1239-1254; Jan. 2001.
Hoskin et al., "Fos expression in the trigeminocervical complex of the cat after stimulation of superior sagittal sinus is reduced by L-NAME" Neuroscience Letters 266:173-176 (May 1999).
Hudson; Basic principles of clinical pharmacology; Clinical Anesthesia; Ch. 11; pp. 239-260; Jan. 2001.
Ibarra, Eduardo; Neuromodulación del Ganglio Esfenopalation para Aliviar los Sintomas del la Cefalea en Raciomos; Boletin El Dolor; vol. 46, No. 16; pp. 12-18; (year of pub. sufficiently earlier than effective US filed and any foreign priority date) 2007 (with English translation).
Iliff et al.; Epoxyeicosanoids as mediators of neurogenic vasodilation in cerebral vessels; Am J Physiol Heart Circ Physiol; vol. 296; pp. 1352-1363; Mar. 20, 2009.
Janes et al.; Anatomy of human extrinsic cardiac nerves and ganglia; American Journal of Cardiology; vol. 57; pp. 299-309; Feb. 1986.
Janzen et al., "Sphenopalatine blocks in the treatment of pain in fibromyalgia and myofascial pain syndrome", Laryngoscope, vol. 107(10): 1420-2 (Oct. 1997).
Karashurov et al.; Evolution of surgical treatment of bronchial asthma; Surgery (Khigurgiia); vol. 11; pp. 57-60; Nov. 1999.
Karashurov et al.; Radio frequency electrostimulation of the gangliated cord of the sympathetic nerve in patients with bronchial asthma; Surgery (Khigurgiia); vol. 1; pp. 44-46; (year of pub. sufficiently earlier than effective US filed and any foreign priority date) 2000 (w/ English Abstract).
Karavis, "The neurophysiology of acupuncture: a viewpoint", Acupuncture in Medicine, vol. 15(1): 33-42 (May 1997).
Kim et al.; Sympathectomy: Open and Thoracoscopic; In: Surgical Management of Pain; Thieme Medical Publishers, Inc.; RD 595.5. 587; Chapter 55; Jan. 2002.
Kittrelle et al., "Cluster headache. Local anesthetic abortive agents", Arch Neurol, vol. 42(5): 496-8 (May 1985).
Kosaras et al.; Sensory innervation of the calvarial bones of the mouse; The Journal of Comparative Neurology (John Wiley & Sons); 48 pgs.; Mar. 2009.
Kudrow et al., "Rapid and sustained relief of migraine attacks with intranasal lidocaine: preliminary findings", Headache, vol. 35(2): 79-82 (Feb. 1995).
Kudrow, "Natural history of cluster headaches—part 1 outcome of drop-out patients", Headache, vol. 22: 203-6 (Sep. 1982).
Kushiku et al.; Upregulation of Immunoreactive Angiotensin II Release and Angiotensinogen mRNA Expression by High-Frequency Preganglionic Stimulation at the Canine Cardiac Sympathetic Ganglia; Circ Res.; 88; pp. 110-116; Jan. 2001.
Lambert et al.; Comparative effects of stimulation of the trigeminal ganglion and the superior sagittal sinus on cerebral blood flow and evoked potentials in the cat; Brain Research; vol. 453; pp. 143-149; Jun. 1988.
Lebovits et al., "Sphenopalatine ganglion block: clinical use in the pain management clinic", Clin J Pain, vol. 6(2): 131-6 (Jun. 1990).
Levine et al.; Central venous and pulmonary artery catheter monitoring; Critical Care Monitoring from Pre-Hospital to the ICU; pp. 145-158; Jan. 1995.
Maizels et al., "Intranasal lidocaine for treatment of migraine", JAMA, vol. 276(4): 319-21 (Jul. 1996).
Manahan et al., "Sphenopalatine ganglion block relieves symptoms of trigeminal neuralgia: a case report", Nebr Med J, vol. 81(9): 306-9 (Sep. 1996) (abstract).
Mansoor et al.; Ambulatory blood pressure monitoring: technique and application in the study of cardiac dysfunction and congestive heart failure; Congest Heart Fail; vol. 7; pp. 319-324; Nov./Dec. 2001.
Matsumoto et al.; Effective sites by sympathetic beta-andrenergic and vagal nonadrenergic inhibitory stimulation in constricted airways; Am Rev Respir Dis; vol. 132; pp. 1113-1117; Nov. 1985.
Matthey et al.; Bedside catheterization of the pulmonary artery: risks compared with benefits; In Clinical Procedures in Anesthesia and Intensive Care; JB Lippincott Company; vol. 109; pp. 826-834; Nov. 1988.
Meyer et al., "Sphenopalatine ganglionectomy for cluster headache", Arch Otolaryngol, vol. 92(5): 475-84 (Nov. 1970).
Meyerson et al.; Alleviation of Atypical trigeminal pain by stimulation of the gasserian ganglion via an implanted electrode; Acta Neurochirurgica; supp. 30; pp. 303-309; (year of pub. sufficiently earlier than effective US filed and any foreign priority date) 1980.
Moskowitz et al., "Basic mechanisms in vascular headache" Headache 8 (4):801-815 (Nov. 1990).
Moskowitz, Michael; Cluster headache: evidence for a pathophysiologic focus in the superior pericarotid cavernous sinus plexus; Headache; vol. 28; pp. 584-586; Oct. 1988.
Moskowitz; Neurogenic inflammation in the pathophysiology and treatment of migraine; Neurology; vol. 43; suppl. 3; pp. S16-S20; Jun. 1993.
Murphy et al.; Human cardiac nerve stimulation; The Annals of Thoracic Surgery; vol. 54; p. 502; Sep. 1992.
Narouze et al.; Sphenopalatine ganglion radiofrequency ablation for the management of chronic cluster headache; Headache; vol. 49; pp. 571-577; Apr. 2009.
Narouze et al.; Sphenopalatine ganglion stimulation for the acute treatment of intractable migraine; American Academy of Pain Medicine Annual Meeting Abstracts; pp. 226 (Abstract No. 157); Jan. 2009.
Nguyen et al., "Chronic motor cortex stimulation in the treatment of central and neuropathic pain. Correlations between clinical, electrophysiological and anatomical data" Pain 82:245-251 (Sep. 1999).
Onofrio et al., "Surgical treatment of chronic cluster headache", Mayo Clin Proc, vol. 61(7), pp. 537-544 (Jul. 1986).
Panina et al.; Assessment of autonomic tone over a 24-hour period in patients with congestive heart failure: relation between mean heart rate and measures of heart rate variability; Am. H. J.; vol. 129; pp. 748-753; Apr. 1995.
Peterson et al., "Sphenopalatine ganglion block: a safe and easy method for the management of orofacial pain", Cranio, vol. 13(3): 177-81 (Jul. 1995) (abstract).
Phebus et al., "The non-peptide NK-1 receptor antagonist LY303870 inhibits neurogenic dural inflammation in guinea pigs" Life Sciences 60(18):1553-1561 (Mar. 1997).
Pollock et al., "Stereotactic radiosurgical treatment of sphenopalatine neuralgia", J Neurosurg, vol. 87(3): 450-3 (Sep. 1997).
Rao et al., "Effectiveness of temporal pattern in the input to a ganglion: Inhibition in the cardiac ganglion of spiny lobsters", J of

(56) References Cited

OTHER PUBLICATIONS

Neurobiology, vol. 1, No. 2, pp. 233-245 (year of pub. sufficiently earlier than effective US filed and any foreign priority date) 1969 (abstract).
Reder et al., "Sphenopalatine ganglion block in treatment of acute and chronic pain", Diagnosis and treatment of chronic pain, John Wright, publisher, 97-108 (year of pub. sufficiently earlier than effective US filed and any foreign priority date) 1982.
Reuter et al.; Experimental models of migraine; Funct Neurol; suppl. 15; pp. 9-18; (year of pub. sufficiently earlier than effective US filed and any foreign priority date) 2000.
Ruskin, "Contributions to the study of the sphenopalatine ganglion", Laryngoscope, vol. 35(2): 87-108 (Feb. 1925).
Ruskin; Sphenopalatine (nasal) gaglion: remote effects including "psychosomatic" symptons, rage reaction, pain, and spasm; Arch Phys Med Rehabil; vol. 60; pp. 353-359; Aug. 1979.
Ryan et al., "Sphenopalatine ganglion neuralgia and cluster headache: comparisons, contrasts, and treatment", Headache, vol. 17: 7-8 (Mar. 1977).
Saade et al., "Patient-administered sphenopalatine ganglion block", Reg Anesth, vol. 21(1): 68-70 (Jan.-Feb. 1996) (abstract).
Sanders et al., "Efficacy of sphenopalatine ganglion blockade in 66 patients suffering from cluster headache: a 12- to 70-month follow-up evaluation", J Neurosurg., vol. 87(6), pp. 876-880 (Dec. 1997).
Scherlag et al.; Endovascular stimulation within the left pulmonary artery to induce slowing of heart rate and paroxysmal atrial fibrillation; Cardiovascular Research; vol. 54; pp. 470-475; May 2002.
Schulz et al., "Localization of epileptic auras induced on stimulation by subdural electrodes" Epilepsia 38(12) 1321-1329 (Dec. 1997).
Scott et al.; Trigger point injections for chronic non-malignant musculoskeletal pain: a systematic review; Pain Medicine; vol. 10; No. 1; pp. 54-69; Jan. 2009.
Seylaz et al., "Effect of stimulation of the sphenopalatine ganglion on cortical blood flow in the rat", J Cerebr Blood Flow and Metab, vol. 8: 875-8 (Dec. 1988).
Shuster et al., "Treatment of vasomotor rhinitis, trigeminal neuralgia and Sluder's syndrome by irradiation of the sphenopalatine ganglion with helium-neon lasers", Vestin Otorinolaringol, vol. 4: 35-40 (Jul.-Aug. 1988).
Sinkjaer et al., "Electroneurography", Encyclopedia of Medical Devices and Instrumentation, Second Edition: pp. 109-132 (Apr. 2006).
Sluder, "The syndrome of sphenopalatine ganglion neuralgia", Am J Medicament Sci, vol. 111: 868-878 (year of pub. sufficiently earlier than effective US filed and any foreign priority date) 1910.
Sluder; The anatomical and clinical relations of the sphenopalatine (Meckel's) ganglion to the nose and its accessory sinuses; NY Med. J.; vol. 90; pp. 293-298; Aug. 1909.
Steude; Percutaneous electro stimulation of the trigeminal nerve in patients with atypical trigeminal neuralgia; Neurochirurgia; vol. 21; pp. 66-69; Mar. 1978.
Storer et al., "Microiontophoretic application of serotonin (5HT) 1B/1D agonists inhibits trigeminal cell firing in the cat" Brain 120:2171-2177 (Dec. 1997).
Strassman et al., "Sensitization of meningeal sensory neurons and the origin of headaches" Nature 384:560-563 (Dec. 1996).
Suzuki et al., "Selective electrical stimulation of postganglionic cerebrovascular parasympathetic nerve fibers originating from the sphenopalatine ganglion enhances cortical blood flow in the rat", J Cerebr Blood Flow and Metab, vol. 10: 383-391 (May 1990).
Suzuki et al.; Trigeminal fibre collaterals storing substance P and calcitonin gene-related peptide ; Neuroscience; vol. 30; No. 3; pp. 595-604; (year of pub. sufficiently earlier than effective US filed and any foreign priority date) 1989.
Taub et al., "Chronic electrical stimulation of the gasserian ganglion for the relief of pain in a series of 34 patients", J Neurosurg, vol. 86: 197-202 (Feb. 1997).
Teerlink et al.; Hemodynamic variability and circadian rhythm in rats with heart failure: role of locomotor activity; Am. J. Physiol.; vol. 264; pp. H2111-H2118; Jun. 1993.
The Cleveland Clinic Foundation; Thalamic Stimulation and Trigeminal Neuralgia; Neuroscience Pathways; March (Spring) 1998 newsletter; pp. 1-2.
Toda et al.; Cerebral blood flow regulation by nitric oxide: recent advances; Pharmacol Rev; vol. 61; No. 1; pp. 62-97; Mar. 2009.
Van Horne et al.; Multichannel semiconductor-based electrodes for in vivo electrochemical and electrophysiological studies in rat CNS; Neuroscience Letters; vol. 120; pp. 249-252; Nov. 1990.
Vitek; Mechanisms of deep brain stimulation: excitation or inhibition; Movement Disorders; vol. 17; supp. 3; pp. S69-S72; Mar.-Apr. 2002.
Walters et al.; Cerebrovascular projections from the sphenopalatine and otic ganglia to the middle cerebral artery of the cat; Stroke; vol. 17; pp. 488-494; May-Jun. 1986.
Witte et al.; Experimental heart failure in rats: effects on cardiovascular circadian rhythms and on myocardial ?-adrenergic signaling; Cardiovasc Res; vol. 47; pp. 350-358; Aug. 2000.
Yee et al.; Circadian variation in the effects of aldosterone blockade on heart rate variability and QT dispersion in congestive heart failure; J. Am. Coll. Cardiol.; vol. 37; pp. 1800-1807; Jun. 2001.
Young, "Electrical stimulation of the trigeminal nerve root for the treatment of chronic facial pain", J Neurosurg, vol. 83: 72-78 (Jul. 1995).
Zarembinski et al.; Sphenopalatine ganglion block in traumatic trigeminal neuralgia and the outcome to radiosurgical ablation; American Academy of Pain Medicine Annual Meeting Abstracts; pp. 200 (abstract No. 102); Jan.-Feb. 2009.
Levin; U.S. Appl. No. 14/667,384 entitled "Apparatus for treating cerebral neurovascular disorders including headaches by neural stimulation,", filed Mar. 24, 2015.
Vollmer et al.; Adrenal medullary catecholamine secretion patterns in rats evoked by reflex and direct neural stimulation; Clinical and Experimental Hypertension; V22(7&8); pp. 705-715; Oct.-Nov. 2000.
Fletcher et al.; U.S. Appl. No. 14/849,351 entitled "Approval per use implanted neurostimulator,", filed Sep. 9, 2015.
Boling et al.; U.S. Appl. No. 14/858,904 entitled "Implantable neurostimulator with integral hermetic electronic enclosure, circuit substrate, monolithic feed-through, lead assembly and achoring mechanism,", filed Sep. 18, 2015.

\* cited by examiner

INTEGRATED DELIVERY AND VISUALIZATION TOOL FOR A NEUROMODULATION SYSTEM

CROSS REFERENCE TO RELATED APPLICATIONS

This application is a continuation of U.S. application Ser. No. 13/784,452, filed Mar. 4, 2013, now U.S. Pat. No. 8,781,574, which is a divisional of U.S. application Ser. No. 12/649,119, filed Dec. 29, 2009, now U.S. Pat. No. 8,412,336, which application claims the benefit under 35 U.S.C. 119 of U.S. Provisional Application No. 61/141,179, filed Dec. 29, 2008, titled "INTEGRATED DELIVERY AND VISUALIZATION TOOL FOR A NEUROMODULATION SYSTEM." These applications are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention relates generally to a surgical tool and visualization method for delivering a therapy delivery device to craniofacial regions, and more specifically to a surgical tool and integral visualization method for delivery of a neurostimulator device to the pterygopalatine fossa (PPF).

BACKGROUND OF THE INVENTION

Electrical stimulation of peripheral and central neural structures has shown increased interest due to the potential benefits it may provide to individuals suffering from many neurological and behavioral diseases. Many of these therapies today are not well accepted due to the invasive nature of the therapy, even though the efficacy is quite good. This has created a need for less invasive therapies that are directed toward patient and physician clinical needs.

Headaches are one of the most debilitating ailments that afflict millions of individuals worldwide. The specific pathophysiology of headaches is unknown. Known sources of headache pain consist of trauma, vascular, autoimmune, degenerative, infectious, drug and medication-induced, inflammatory, neoplastic, metabolic-endocrine, iatrogenic, musculoskeletal and myofacial causes. Also, even though the possible underlying cause of the headache pain is identified and treated, the headache pain may persist.

Currently, the sphenopalatine (pterygopalatine) ganglion (SPG) is a target of manipulation in clinical medicine to treat headaches. The SPG is an extracranial neuronal center located behind the nose. It consists of parasympathetic neurons that innervate (in part) the middle cerebral and anterior cerebral blood vessels, the facial blood vessels, and the lacrimal glands. The SPG also consists of sympathetic and sensory nerve fibers that pass through the SPG in route to their end organs. Manipulation of the SPG is mostly performed in attempted treatments of severe headaches, such as cluster headaches or chronic migraines.

Various clinical approaches have been used for over 100 years to modulate the function of the SPG to treat headaches. These procedures vary from least invasive (e.g. transnasal anesthetic blocks) to much more invasive (e.g. surgical ganglionectomy) as well as procedures such as surgical anesthetic injections, ablations, gamma knife and cryogenic surgery. Most of these procedures have very good short term efficacy outcomes (days to months), however these results are usually temporary and the headache pain returns. A chronically implanted SPG neurostimulator may provide much better long term efficacy in these patients.

SUMMARY OF THE INVENTION

In one embodiment, a method of delivering a neurostimulator to within close proximity of a sphenopalatine ganglion is provided, comprising making an incision over the anterior maxilla, inserting a delivery tool having an integrated visualization system into the incision, visualizing tissue near a distal portion of the delivery tool with the visualization system, advancing the delivery tool sub-periosteally at a lateral edge of a zygomaticomaxillary buttress region towards a pterygopalatine fossa, and delivering the neurostimulator in close proximity to the sphenopalatine ganglion.

The method can further comprise the step of elevating a periosteum away from the anterior maxilla with the delivery tool to expose a zygomaticomaxillary buttress region prior to the advancing step. In some embodiments, the advancing step further comprises advancing the delivery tool posteriorly, medially, and superiorly towards the pterygopalatine fossa.

In one embodiment, the delivery tool includes a contoured distal portion that is shaped and configured to maintain contact with a posterior maxilla and elevate a periosteum off of the posterior maxilla to avoid soft tissue dissection. The contoured distal portion can have a thickness of between 2-5 mm, for example. In some embodiments, the contoured distal portion has an elliptical cross-section.

In one embodiment, the visualization system comprises a fiberscope.

In some embodiments, the method further comprises the step of illuminating the delivery tool with a light source placed within a nasal cavity and positioned close to or within a sphenopalatine foramen.

A delivery tool configured to deliver a neurostimulator into a patient is also provided, comprising a handle portion, an elongate shaft comprising a contoured distal portion, the contoured distal portion shaped and configured to maintain contact with a posterior maxilla and elevate a periosteum off of the posterior maxilla to avoid soft tissue dissection, a visualization system embedded in the elongate shaft, and an insertion groove on the elongate shaft configured to deploy the neurostimulator.

In some embodiments, the insertion groove is recessed into the elongate shaft. In other embodiments, the insertion groove is located on an opposing edge of the delivery tool from the visualization system, allowing for visualization of the deployment of the neurostimulator.

In some embodiments, the visualization system is a fiberscope. In other embodiments, the visualization system comprises a light source contained in the handle portion.

In one embodiment, the delivery tool further comprises a lens embedded at the distal portion, the lens constructed to allow for a focal length of between 2-15 mm.

In other embodiments, the visualization system is configured to highlight differences between soft tissue and bone. In another embodiment, the visualization system comprises an electronic chip positioned within the distal portion and configured to provide video and/or still images to be sent to a viewing system.

In one embodiment, the delivery tool further comprises an external light source configured to provide transillumination of the delivery tool. In another embodiment, the delivery tool further comprises an aperture configured to dispense a fluid to a distal end of the delivery tool. The delivery tool can further comprise a touch sensitive button coupled to the aperture, wherein a quick press of the button releases a bolus of fluid and a long press of the button releases a continuous stream of fluid.

In some embodiments, the delivery tool further comprises a bifurcated distal dissecting tip having a lens positioned between the dissecting tips.

In additional embodiments, the delivery tool further comprises a tissue clearance tip around the visualization system configured to provide increased tissue clearance around the visualization system.

In some embodiments, the contoured distal portion has a thickness of between 2-5 mm. In other embodiments, the contoured distal portion has an elliptical cross-section.

A method of treating a neurological disorder is also provided, comprising making an incision over an anterior maxilla, inserting a delivery tool having an integrated visualization system into the incision, visualizing tissue near a distal portion of the delivery tool with the visualization system, advancing the delivery tool sub-periosteally at a lateral edge of the zygomaticomaxillary buttress region towards the pterygopalatine fossa, delivering the neurostimulator in close proximity to the sphenopalatine ganglion, and applying an electrical current from the neurostimulator to the sphenopalatine ganglion to treat the neurological disorder.

In some embodiments, the method further comprises the step of elevating a periosteum away from the anterior maxilla with the delivery tool to expose a zygomaticomaxillary buttress region prior to the advancing step.

In another embodiment, the delivery tool includes a contoured distal portion that is shaped and configured to maintain contact with a posterior maxilla and elevate a periosteum off of the posterior maxilla to avoid soft tissue dissection.

In some embodiments, the neurological disorder is headache.

DETAILED DESCRIPTION OF THE INVENTION

Figure 1:
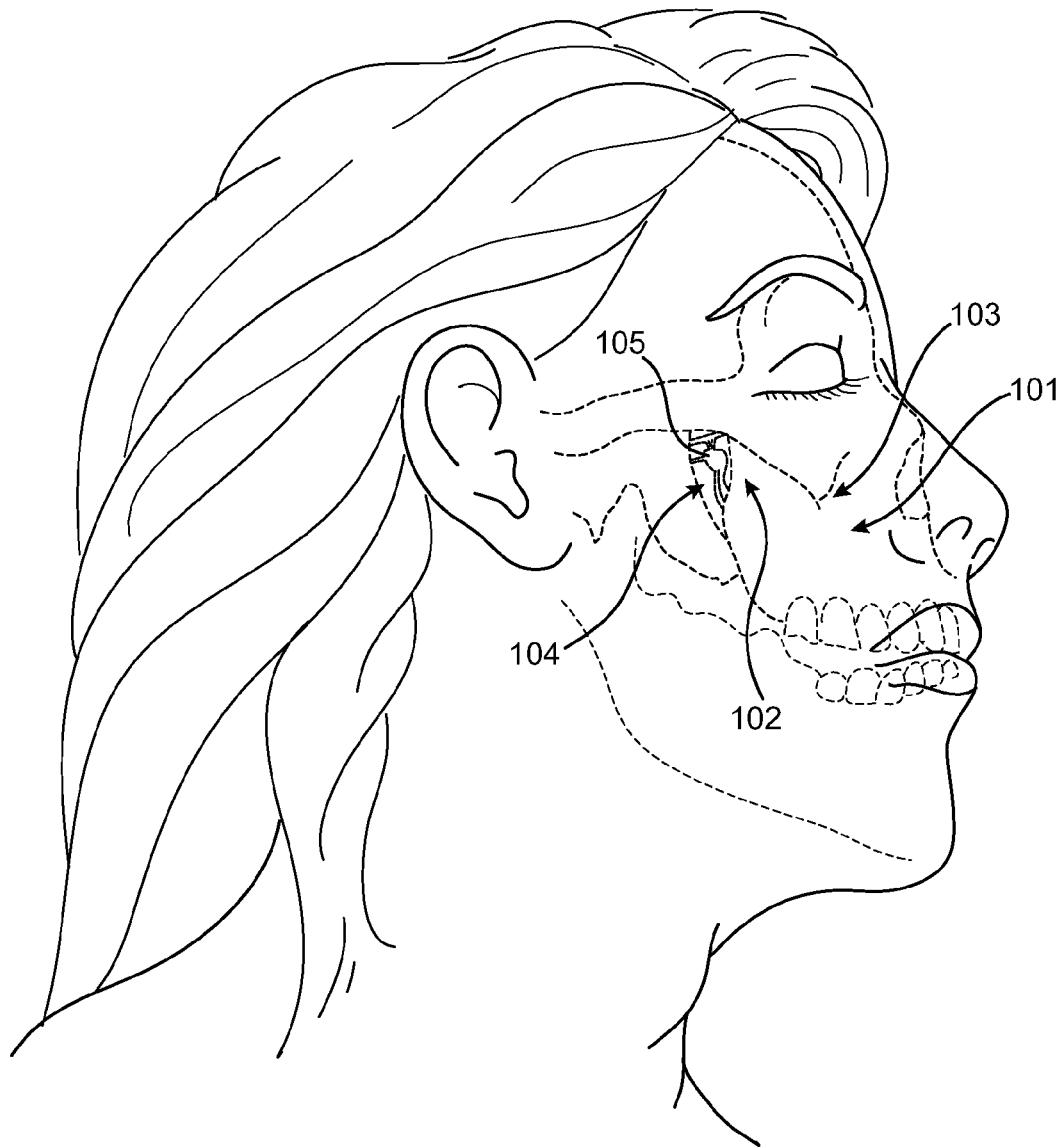
FIG. 1 is a lateral looking view of the target anatomy.
Figure 2:
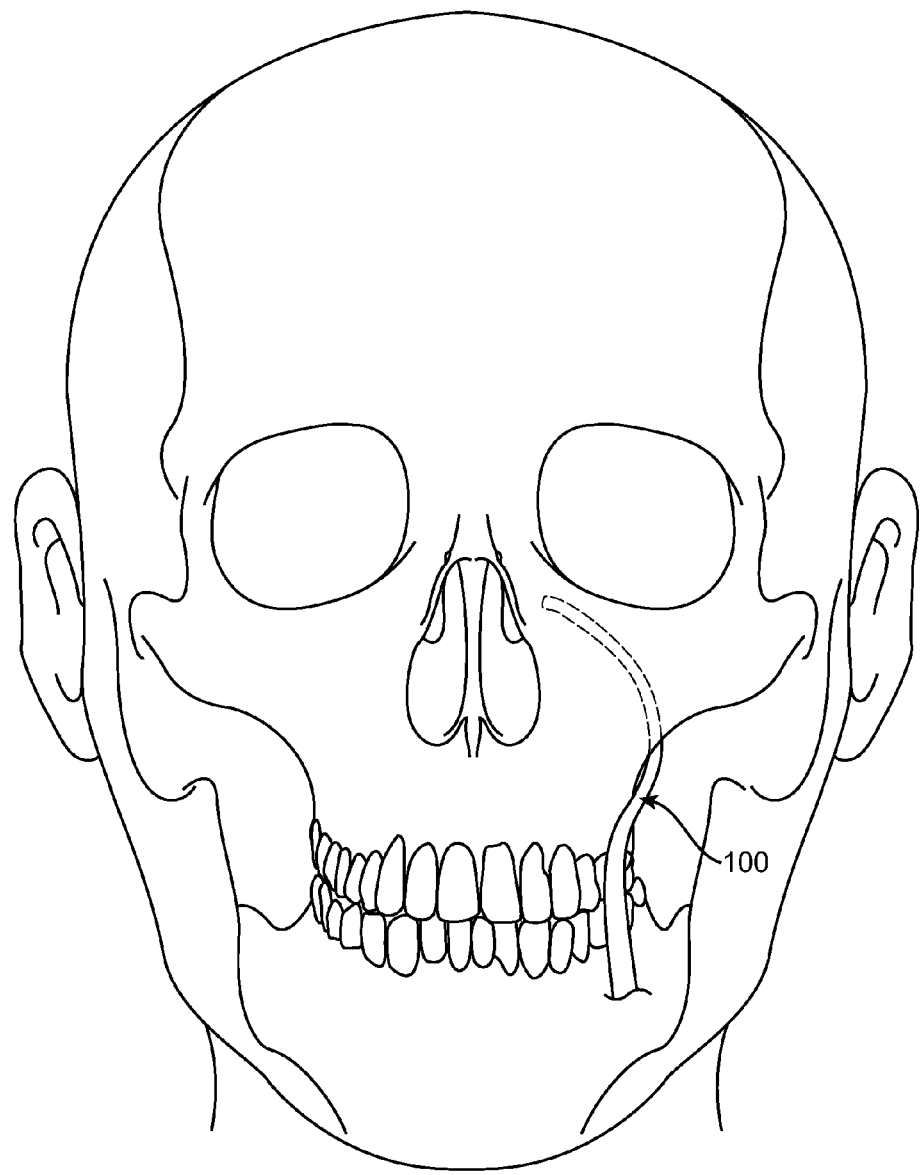
FIG. 2 is a front looking view of a delivery and visualization tool.

FIG. 2 illustrates an embodiment of an integrated delivery and visualization tool 100 shown positioned within the craniofacial anatomy. The tool can be used in aided delivery of a small neurostimulator for the treatment of chronic headaches. The tool is designed and constructed to elevate and or dissect the periosteum and soft tissue, and to visualize the intended anatomy, as illustrated in FIG. 1, during delivery of the neurostimulator. The tool is designed to be inserted trans-orally from an incision located on the anterior maxilla 101. The tool can then elevate the periosteum away from the anterior maxilla bone 101 to expose the zygomaticomaxillary buttress region 103. The tool can then be inserted sub-periosteally at the lateral edge of the zygomaticomaxillary buttress and advanced posteriorly, medially, and superiorly towards the PPF 104. The SPG 105, a small extracranial autonomic ganglion, is located within the PPF. The SPG is the intended target for stimulation for the treatment of headaches and other neurological disorders. This tool is designed and configured to deliver the neurostimulator in very close proximity to the SPG, by contacting the SPG directly or by placing the neurostimulator within 1-5 mm of the SPG, such that targeted electrical stimulation or delivery of electrical current from the neurostimulator to the SPG can be accomplished.

Figure 3:
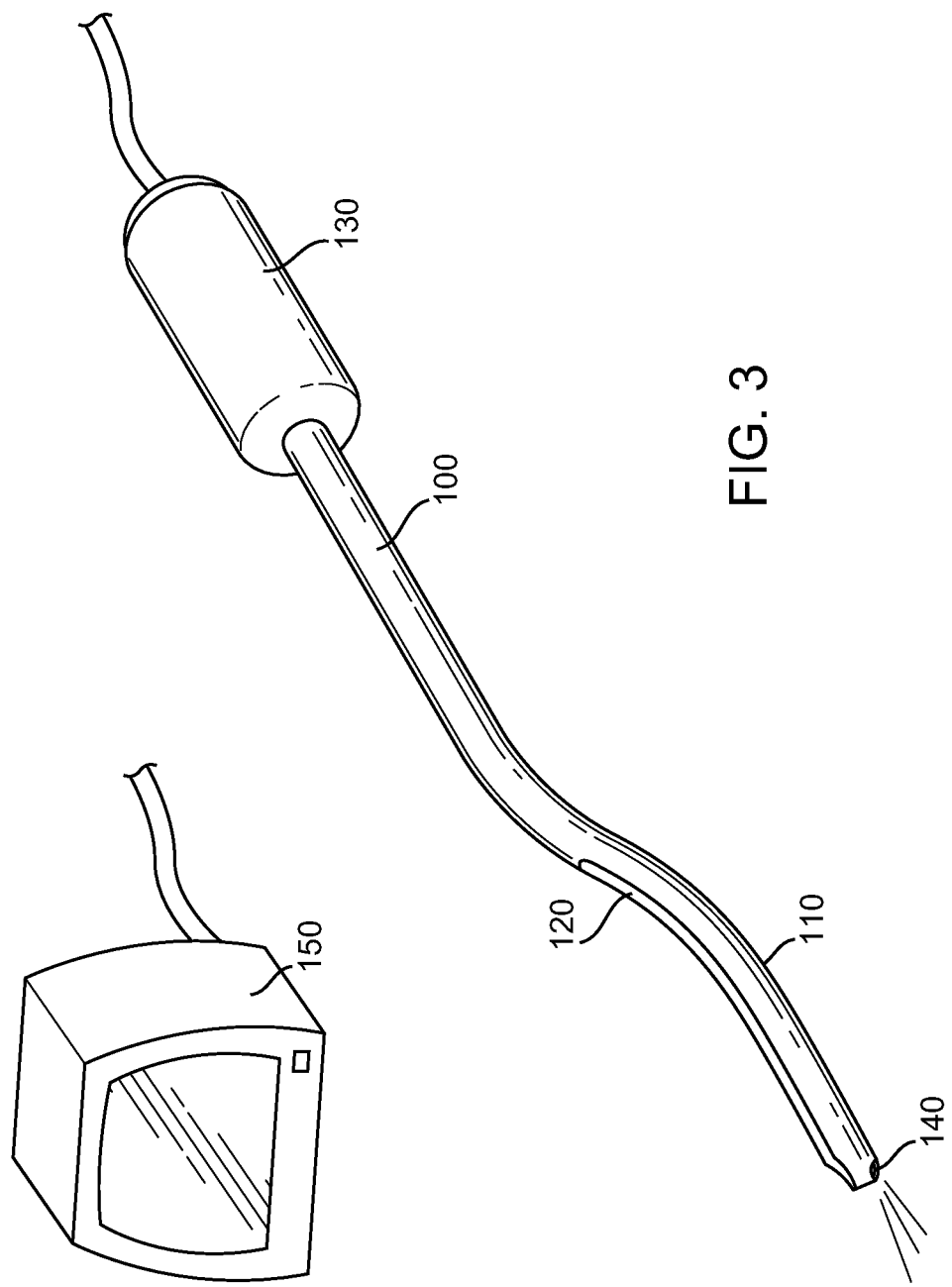
FIG. 3 is an isometric view of the integral delivery and visualization tool.

In one embodiment, as shown in FIG. 3, the tool 100 features an elongate shaft comprising a compound-contoured distal portion 110 with an integral visualization system 140. Using an integral visualization system in the delivery tool advantageously reduces or eliminates radiation exposure in the patient since fewer or no x-rays or fluoroscopy are needed. The tool can be made of surgical grade stainless steel, for example. In one embodiment the tool is approximately 15-40 cm in length, excluding the visualization viewing system attachments. The distal portion 110 of the tool can be shaped and configured such that a user can maintain contact with the posterior maxilla while advancing the tool sub-periosteally to the pterygopalatine fossa. The tool is shaped and designed to maintain bone contact and elevate the periosteum off the bone to avoid soft tissue dissection, which may prevent unwanted soft tissue injury or bleeding during the implantation of a neurostimulator. Additionally, by remaining sub-periosteal, a higher contrast between the bone and the soft tissue overlaying the periosteum can make visualization easier.

In one embodiment, the visualization system comprises a fiberscope 140 embedded into the elongate shaft of the delivery tool, as shown in FIG. 3. The fiberscope allows for both illumination and visualization of tissue near the distal end of the delivery tool. The fiberscope can contain two types of fiber optic bundles, such as fiber optic light bundles for illumination and fiber optic image bundles to relay images to the viewing system. The number of fibers within the fiberscope visualization system is dependent on the overall diameter of each fiber and the overall diameter of the fiberscope, which is dependent on the size and shape of the delivery tool.

In some embodiments, the delivery tool's distal portion 110 can have a thickness of between 2-5 mm, with a fiberscope diameter that corresponds to the thickness of the delivery tool (2-5 mm). More specifically, the distal portion of the tool can be 3 mm thick with a fiberscope diameter of 2 mm. The tool's distal portion 110 can have a radius of curvature ranging from 8 cm to 0.3 cm. In one specific embodiment, the radius of curvature of the distal portion can be approximately 4.5 cm, and in another embodiment, the radius of curvature of the tool's distal portion can be nearly flat. The illumination fibers within the fiberscope can accommodate a number of different light sources, including, but not limited to, white, red, blue, green, infrared, and near infrared light sources. In some embodiments, the light sources are contained within the delivery tool and more specifically within the handle of the delivery tool.

The light sources may be light emitting diodes or other standard light sources that can be contained in the handle of the delivery tool. Also in some embodiments, the light sources are selectable as individual sources or in combination sources used in conjunction. The different light sources may allow for differentiation of different tissue types, for example, bone, fat, blood vessels, and nerves, where blue light is preferred for achieving good contrast between nerves and other tissues.

A lens can also be embedded at the distal portion of the delivery tool, the lens being constructed to allow for maximum viewing angle at the tip of the delivery tool. In some embodiments, the lens can allow for a focal length of between 2-15 mm. More specifically, since the depth of the PPF is variable but likely between 10 and 20 mm deep, and the location of the SPG within the PPF is between 4 and 10 mm from the medial wall of the PPF, a viewing distance or focal length of 5-7 mm will likely cover the range needed with the distal portion of the delivery tool at or just within the opening of the PPF.

The fiberscope can then be attached to a viewing system 150, as shown in FIG. 3. The viewing system 150 can be a standard video display with the necessary electronics to convert the image from the fiberscope to a real time video display. Alternatively, a customized viewing system can be made that includes advanced image processing capabilities to help guide implantation, for example, by highlighting the differences between soft tissue and bone. The advanced image processing may include the ability to detect and process non-visible wavelengths, such as, but not limited to, infrared and near-infrared.

In an alternative embodiment, a separate light source may be used in conjunction with or solely to help illuminate and visualize the target anatomy. The PPF is located behind the nose and is constrained anteriorly by the posterior maxilla, medially by the sphenoid bone, posteriorly by the pterygoid process and laterally open to the infratemporal fossa. Additionally the PPF can be accessed from the nasal cavity via the sphenopalatine foramen or laterally from the infratemporal fossa. A light source can be placed within the nasal cavity and positioned close to or within the sphenopalatine foramen to provide illumination of the tool. The light source can include, but is not limited to, white, red, blue, green, infrared, and near infrared light sources. Additionally, to aid in the placement of the neurostimulator within very close proximity to the SPG, additional working channels can be utilized though the nasal cavity for additional tools to help pull the neurostimulator into the correct placement or make small adjustments to the final location of the neurostimulator.

In an additional embodiment, an external bright light source may also be used in conjunction with or solely to help illuminate and visualize the target anatomy. The PPF is open on its lateral aspect to the infratemporal fossa, thus a bright light may be placed on the external skin, and more specifically, on the cheek or forehead either in or out of a dark room to transilluminate the target anatomy PPF. Transillumination is a procedure used for medical diagnostic purposes to visualize the maxillary and frontal sinuses to rule out any problems in these areas. Since the PPF is located just posterior to the maxillary sinus and inferior to the frontal sinuses, transillumination in this area may provide an adequate light source for visualization of the PPF and more specifically the SPG. The bright light source used can include, but is not limited to, white, red, blue, green, infrared, and near infrared light sources.

The compound-contoured distal portion comprises a curvilinear body having an elliptical cross-section, with a sharpened edge at the distal tip of the curvilinear body that is configured to contact the bone and dissect through the tissue. The distal edge can be configured and shaped to traverse around the zygomaticomaxillary buttress and under the zygomatic bone along the posterior maxilla and into the pterygopalatine fossa, while maintaining contact with the posterior maxilla 102, as labeled in FIG. 1, and lifting the periosteum off the posterior maxilla.

According to this embodiment the tool can also include an insertion groove 120 in the elongate shaft. The insertion groove is recessed into the elongate shaft and configured to guide and/or deploy the neurostimulator into the pterygopalatine fossa to within close proximity of the target neural anatomy, such as the SPG. Once the tool is place in position within the PPF and in close proximity to the SPG, the distal end of the neurostimulator is placed within the proximal portion of the insertion groove on the tool and advanced. The neurostimulator is advanced by pushing the neurostimulator along the insertion groove into the PPF. In one embodiment, the insertion groove 120 is located on the opposing edge of the delivery tool from the fiberscope and fiberscope lens 140, allowing for visualization of the deployment of the neurostimulator into the target anatomy.

Also according to this embodiment, the tool incorporates an ergonomic handle 130 of approximately 6-12 cm in length, varying in diameter from proximal (0.5-3 cm) to distal (0.5-2 cm), with variable methods to provide grip and tactile manual maneuverability, such as circumferential ridges or cross-hatched precut pattern into the surgical grade stainless steel. In one embodiment, the handle and shaft of the delivery tool can contain the flexible fiberscope within the body of the tool.

Figure 4A:
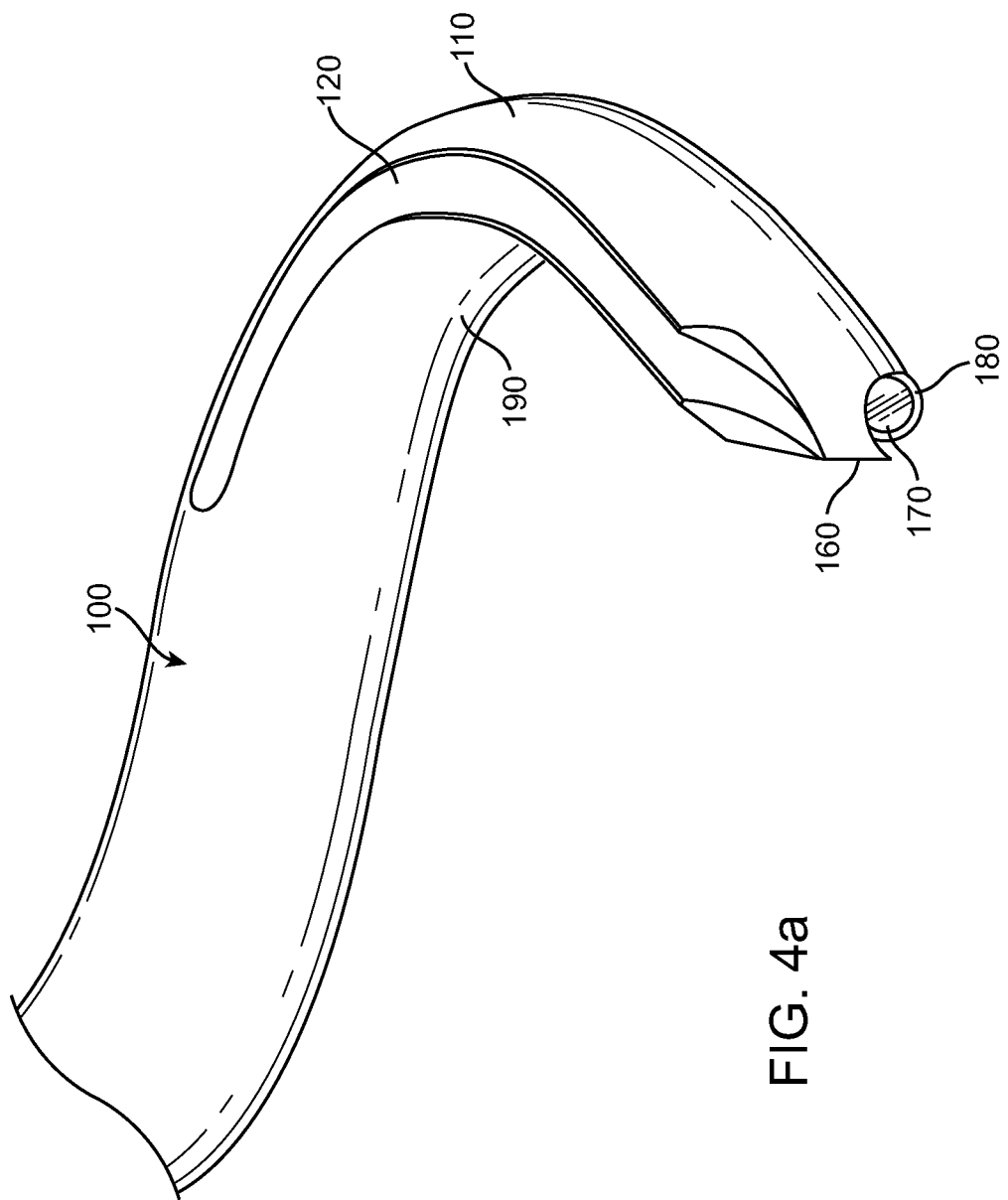
FIG. 4a is a detailed isometric view of the distal tip of the tool.

FIG. 4a shows a close-up view of the curvilinear geometry of the distal portion 110 of the integral delivery and visualization tool 100. As illustrated in FIG. 4a, the tool incorporates an insertion or deployment groove 120, a tissue dissecting tip 160, an integral fiberscope visualization system 170, and an aperture 180. The aperture can be used to dispense saline to the distal tip of the tool, providing a gap between the tissue and the visualization system's lens. A piece of plastic (or other transparent material) can also provide a gap between the lens and the tissue. The aperture could also be used to remove fluid from the tip of the device, for example, blood.

The delivery of fluid through the aperture can be done from a syringe based system, which can be attached to the delivery tool. However, in one embodiment, the delivery and visualization tool maintains a refillable volume of fluid within the handle. The fluid can be deployed into the visualization field using an integral button on the handle of the delivery tool. The button can be touch sensitive, such that a quick press releases a bolus of fluid into the visualization field, and a long press delivers a continuous stream of fluid into the visualization field to clear and create tissue separation for increased visualization. Alternatively, fluid can be delivered by a control system attached to the tool, or manually by the user, for example, using standard IV drip lines. The stored fluid can be normal saline, or other physiological solutions, such as sterile water. The stored fluid can also be or contain a therapeutic or diagnostic agent, such as but not limited to vasocontrictive agents or a local anesthetic, such as lidocaine, or other types of drugs used to create local anesthetic blocks. The fluid can be delivered from the distal tip of the tool through a larger lumen that contains the fiberscope, according to some embodiments. Alternatively, the fluid can be delivered to the tip of the tool through a small lumen or catheter that is integrated to the shaft of the tool. The same system can also be used to remove fluid, for example, blood or saline, using external suction.

In one embodiment, the distal portion 110 of the tool also incorporates a curvilinear geometry along the axis of the tool. The curvilinear geometry can range between 2.5 cm and 7.5 cm. The distal curve of the tool is designed to allow maximal engagement of the posterior maxilla as the delivery tool is advanced posteriorly, medially and superiorly into the PPF of human patients of different anatomical sizes, while minimizing tissue damage by dissecting the plane between the bone and the periosteum. The sculpted distal portion of the tool tapers to the distal tip, which maintains contact with the bone and can be generally elliptically shaped in cross-section, as shown in FIG. 4b.

Figure 4B:
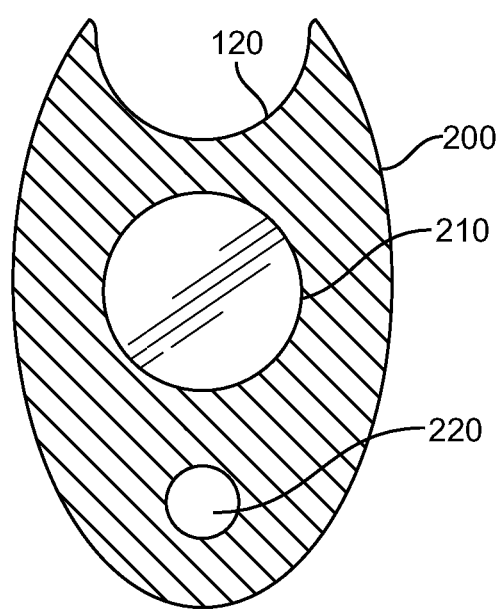
FIG. 4b is a cross-section of the distal tip of the tool.

In one embodiment, as shown in FIG. 4b, the embedded fiberscope can be located centrally within a lumen 220 in the cross-section of a delivery tool 200. Also according to this embodiment, the aperture for fluid delivery has a separate lumen 220. In this embodiment each lumen runs the length of the delivery tool. The lumen for the fiberscope and aperture can be located away from the insertion or deployment groove 120.

In FIG. 4b, the distal tip of the integral delivery and visualization system is adapted to taper to a sharp edge that is similar to standard surgical periosteal elevators. At the distal tip, the final 5-15 mm of the tip may have an increased curvature in the same plane as the distal portion curvature of the tool. This increased curvature at the tip is done to allow greater contact with the posterior maxilla as the delivery tool is advanced toward the PPF. Also, this curvature creates increased amount of tissue separation that allows for increased amount of visualization of the target anatomy. Also according to this embodiment and the primary embodiment, as the distal tip tapers to the distal edge, the lumen for the fiberscope is stopped such that the distal edge and the fiberscope lens are not in the same plane, but the fiberscope lens is more proximal from the distal tip. Alternatively, a clear glass can be used to fill in the gap between the distal edge and the lens from the fiberscope, or the gap can be filled in by a custom made lens. In yet another embodiment, individual fibers from the fiberscope can extend to the distal edge of the tool so that no gap exists between the individual fibers and the lens at the distal edge of the tool.

Figure 5:
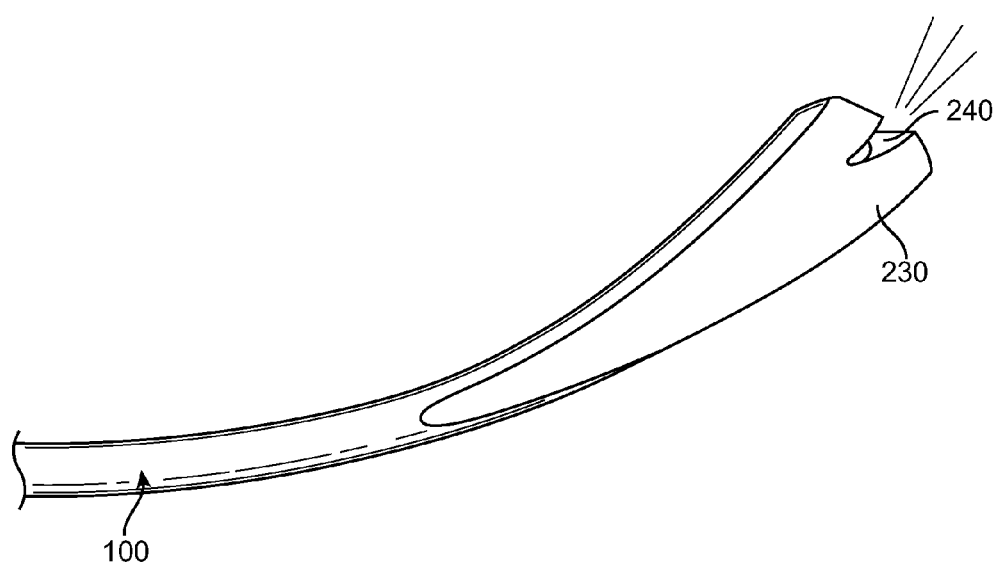
FIG. 5 is an isometric view of an alternate embodiment of a bifurcated distal tip of the tool.

In an alternative embodiment, as illustrated in FIG. 5, the tool 100 may include a bifurcated distal dissecting tip 230, with a lens 240 centered or arranged between the tissue dissecting members. Alternate embodiments of the tool include various tips of various shapes and configurations to either bluntly or sharply dissect the periosteum from the bone and include visualization of the target anatomy.

In other embodiments of the tool, the shaft and tool tip can be manufactured from various other materials: metals such as titanium and rigid polymers such as PEEK, polycarbonate, or nylon. The tool may also be made from ceramics such as aluminum oxide or zirconium oxide. Additionally, the tool may be made from combinations of metals, ceramics, plastics or plastic composites. Alternate embodiments of the tool include tips that are removable from the tool for disposal or exchanged for different tip, such as tips with different curvatures, dissecting edges, and visualization lens.

Another embodiment of the integrated delivery and visualization tool includes a fiber optic scope that is used as auxiliary equipment to the tool and engages and disengages as required. The fiber optic scope in this embodiment is used to visualize surrounding tissue and the SPG as the tool advances across the posterior maxilla and into the PPF.

Figure 6:
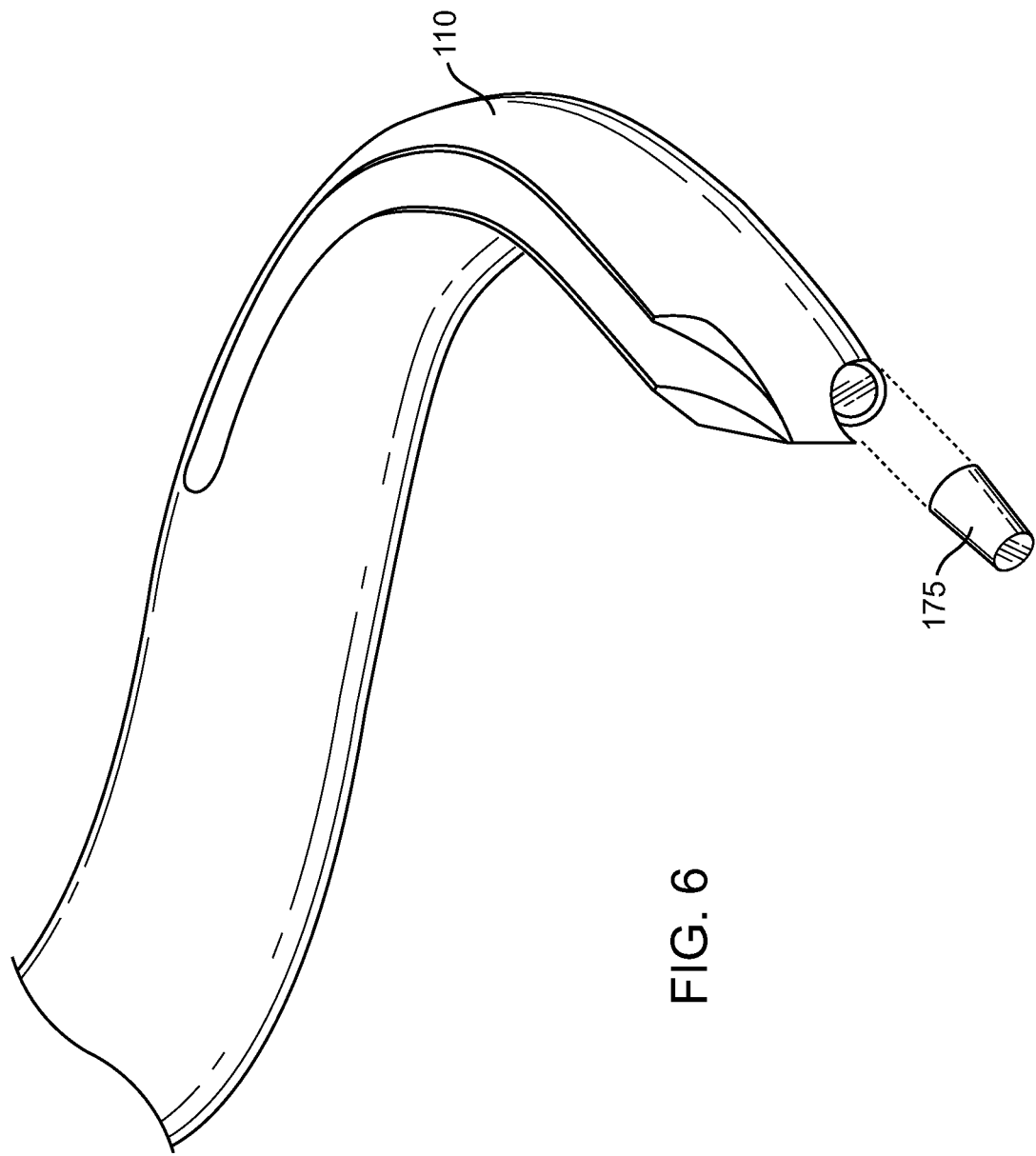
FIG. 6 is an isometric view of a lens covering shown engaging the fiber lens on the distal tip of the tool.

As illustrated in FIG. 6, a distal portion 110 of the tool can support an additional clearance tip 175 configured to provide increased tissue clearance around the fiberscope visualization system for greater visualization of the target tissue. The tissue clearance tip 175 can be fitted onto the tip of the fiberscope and can be made from either polymers or plastics that have an optically transparent and non distorting finish to provide the greatest visualization of the surrounding tissue.

Figure 7:
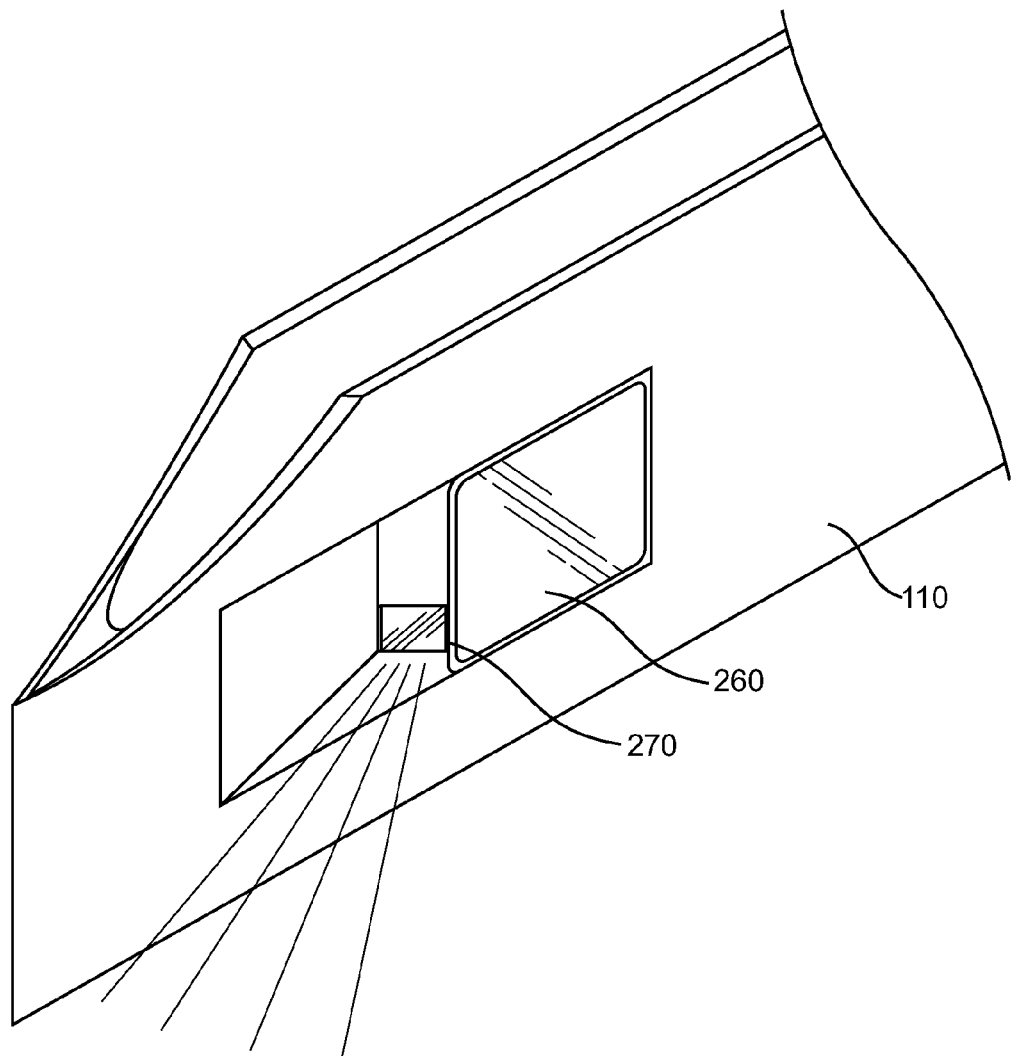
FIG. 7 is an enlarged isometric view of an alternate embodiment of the distal tip housing a digital video camera.

As illustrated in FIG. 7, an alternate embodiment of the distal portion 110 of the tool includes a miniature digital electronic chip 260 and a miniature light emitting diode 270, either integral within the distal portion of the integrated delivery and visualization tool or on the elongate shaft of the tool, and containing a lens or prism and lens that is directed forward to visualize the target anatomy. The digital chip can provide video and or still images to be sent to a viewing system. The digital chip can be linked to the viewer system either using a wired or wireless connection. The viewing system can be a standard external video display, and small handheld display, or integrated into a heads up display located on a pair of glasses worn by the user. The viewing system can be used as part of any or all of the embodiments described in this application.

In an alternate embodiment, either in addition to or instead of the visualization system, a contact switch can be included at or near the distal portion of the delivery tool, such that it is nominally in contact with bone. The switch could be mechanical, like a reed switch, or electrical, like a capacitive proximity sensor, and can communicate contact with bone to the user when deformed. Communication can be achieved audibly, for example with an alarm, visibly, for example with a light, or mechanically, for example with a button that pops up. Further, if a visualization system is being used, an alert can be communicated on the monitoring screen.

In an additional embodiment, the tool may be designed to allow safe transmission of RF (radiofrequency) energy without affecting the safety of the patient or efficacy of the tool. Transmitting RF energy to achieve hemostasis by coagulating bleeding vessels is a common surgical technique. By designing the tool to safely transmit RF energy, the surgeon can coagulate undesirably bleeding vessels and or tissues without removing the tool. In order to achieve this, all but the areas desired for RF delivery would be electrically insulated from the patient and the user to prevent RF energy from affecting undesired areas in the patient or the user.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A delivery tool configured to deliver a neurostimulator into a patient, comprising:
   a handle portion;
   an elongate shaft comprising a curved distal portion, the curved distal portion being shaped and configured to maintain contact with a posterior maxilla of the patient and elevate a periosteum of the patient off of the posterior maxilla to avoid soft tissue dissection;
   a bifurcated distal dissecting tip having a lens positioned between the dissecting tips;
   a visualization system embedded in the elongate shaft; and
   an insertion groove on the elongate shaft configured to deploy the neurostimulator.

2. The delivery tool of claim 1, wherein the insertion groove is recessed into the elongate shaft.

3. The delivery tool of claim 1 wherein the insertion groove is located on an opposing edge of the delivery tool from the visualization system, allowing for visualization of the deployment of the neurostimulator.

4. The delivery tool of claim 1 wherein the visualization system is a fiberscope.

5. The delivery tool of claim 1 wherein the visualization system comprises a light source.

6. The delivery tool of claim 1 further comprising a lens embedded at the distal portion, the lens constructed to allow for a focal length of between 2-15 mm.

7. The delivery tool of claim 1 wherein the visualization system is configured to highlight differences between soft tissue and bone.

8. The delivery tool of claim 1 wherein the curved distal portion has a thickness of between 2-5 mm.

9. The delivery tool of claim 1 wherein the curved distal portion has an elliptical cross-section.

10. A delivery tool configured to deliver a neurostimulator into a patient, comprising:
    a handle portion;
    an elongate shaft comprising a contoured distal portion, the contoured distal portion being shaped and configured to maintain contact with a posterior maxilla and elevate a periosteum off of the posterior maxilla to avoid soft tissue dissection;
    a bifurcated distal dissecting tip having a lens positioned between the dissecting tips;
    a visualization system embedded in the elongate shaft; and
    an insertion groove on the elongate shaft configured to deploy the neurostimulator.

11. The delivery tool of claim 10, wherein the insertion groove is recessed into the elongate shaft.

12. The delivery tool of claim 10 wherein the insertion groove is located on an opposing edge of the delivery tool from the visualization system, allowing for visualization of the deployment of the neurostimulator.

13. The delivery tool of claim 10 wherein wherein the visualization system is a fiberscope.

14. The delivery tool of claim 10 wherein the visualization system comprises a light source.

15. The delivery tool of claim 10 further comprising a lens embedded at the distal portion, the lens constructed to allow for a focal length of between 2-15 mm.

16. The delivery tool of claim 10 wherein the visualization system is configured to highlight differences between soft tissue and bone.

17. The delivery tool of claim 10 wherein the distal portion has a thickness of between 2-5 mm.

18. The delivery tool of claim 10 wherein the distal portion has an elliptical cross-section.

* * * * *